US011490723B2

(12) United States Patent
Truong et al.

(10) Patent No.: US 11,490,723 B2
(45) Date of Patent: Nov. 8, 2022

(54) END EFFECTOR WITH EMBEDDED POWER SOURCE

(71) Applicant: L'OREAL, Paris (FR)

(72) Inventors: Lily Truong, Redmond, WA (US); Zane Bowman Allen Miller, Seattle, WA (US); JoHannes Paul, Duvall, WA (US); Geoffrey F. Deane, Bellevue, WA (US)

(73) Assignee: L'OREAL, Paris (FR)

( * ) Notice: Subject to any disclaimer, the term of this patent is extended or adjusted under 35 U.S.C. 154(b) by 690 days.

(21) Appl. No.: 16/206,703

(22) Filed: Nov. 30, 2018

(65) Prior Publication Data

US 2020/0170399 A1 Jun. 4, 2020

(51) Int. Cl.
*A61H 7/00* (2006.01)
*A61H 23/00* (2006.01)
(Continued)

(52) U.S. Cl.
CPC ............ *A46B 13/02* (2013.01); *A46B 5/0095* (2013.01); *A46B 9/06* (2013.01); *A46B 11/001* (2013.01); *A46B 13/003* (2013.01); *A46B 13/008* (2013.01); *A46B 13/023* (2013.01); *A46B 13/04* (2013.01); *A46B 15/0004* (2013.01); *A46B 15/0036* (2013.01); *A61H 7/005* (2013.01); *A61H 23/00* (2013.01); *A61H 23/0254* (2013.01); *A61N 5/0616* (2013.01); *B25J 19/005* (2013.01); *B25J 19/0025* (2013.01); *A46B 2200/102* (2013.01);
(Continued)

(58) Field of Classification Search
CPC ..... A46B 13/02; A46B 11/001; A46B 13/003; A46B 15/0004; A46B 15/0036; A46B 2200/102; A46B 2200/1006; A46B 5/0095; A46B 9/06; A46B 13/008; A46B 13/023; A46B 13/04; B25J 19/0025; B25J 19/005; A61H 7/002; A61H 7/004; A61H 7/005; A61H 23/00; A61H 23/0254; A61N 5/0616; A61N 2005/063; A61N 2005/0644

See application file for complete search history.

(56) References Cited

U.S. PATENT DOCUMENTS 5,471,695 A * 12/1995 Aiyar ..................... A46B 13/02
601/72
5,511,270 A * 4/1996 Eliachar ................. A46B 13/02
601/72
(Continued)

FOREIGN PATENT DOCUMENTS

EP 3141171 A1 3/2017

OTHER PUBLICATIONS

International Search Report and Written Opinion dated Jun. 24, 2020, issued in corresponding International Application No. PCT/US2019/059640, filed Nov. 4, 2019, 20 pages.

*Primary Examiner* — Tu A Vo
(74) *Attorney, Agent, or Firm* — Christensen O'Connor Johnson Kindness PLLC

(57) ABSTRACT

End effectors and systems including end effectors including embedded batteries and auxiliary components powered by the batteries are described. In an example, the end effector includes a base portion coupleable to a motor carried by an appliance that is separate from the end effector; and a battery disposed in the base portion configured to power an auxiliary component of the end effector.

12 Claims, 7 Drawing Sheets

(51) Int. Cl.
  *A46B 13/02*   (2006.01)
  *A46B 11/00*   (2006.01)
  *A46B 15/00*   (2006.01)
  *A46B 5/00*    (2006.01)
  *A46B 9/06*    (2006.01)
  *A46B 13/04*   (2006.01)
  *A61N 5/06*    (2006.01)
  *A46B 13/00*   (2006.01)
  *B25J 19/00*   (2006.01)
  *A61H 23/02*   (2006.01)

(52) U.S. Cl.
  CPC . *A46B 2200/1006* (2013.01); *A61N 2005/063* (2013.01); *A61N 2005/0644* (2013.01)

(56) References Cited

U.S. PATENT DOCUMENTS

| | | | | |
|---|---|---|---|---|
| 5,647,841 A * | 7/1997 | Groenewold | ......... | A46B 13/04 15/29 |
| 9,198,502 B2 * | 12/2015 | Barnes | ............... | A46B 15/0034 |
| 2006/0135319 A1 * | 6/2006 | Berman | ............ | A61H 15/0085 482/11 |
| 2006/0135891 A1 * | 6/2006 | Jordan | .............. | A61H 23/0263 601/20 |
| 2007/0123808 A1 * | 5/2007 | Rhoades | ............. | A46B 5/0016 601/73 |
| 2008/0014011 A1 * | 1/2008 | Rossen | ................. | A61H 15/02 401/195 |
| 2008/0125680 A1 * | 5/2008 | Richmond | ........ | A61H 23/0263 601/72 |
| 2009/0177125 A1 * | 7/2009 | Pilcher | .............. | A46B 15/0034 601/18 |
| 2010/0222719 A1 * | 9/2010 | Cowie | ................... | A61H 7/005 601/46 |
| 2011/0041864 A1 * | 2/2011 | Kalman | ................ | A45D 24/10 132/120 |
| 2014/0107543 A1 * | 4/2014 | Pazouki | ............... | A61H 7/005 601/72 |
| 2014/0135798 A1 * | 5/2014 | David | ................. | A61N 5/0624 606/131 |
| 2015/0182078 A1 * | 7/2015 | Miller | ................. | A46B 13/008 15/22.1 |
| 2015/0182290 A1 * | 7/2015 | Grez | ........................ | A61F 7/00 600/10 |
| 2015/0190299 A1 * | 7/2015 | Jurna | .................... | A61H 7/005 601/114 |
| 2015/0333609 A1 * | 11/2015 | Lattanzi | .................. | H02K 1/34 310/38 |
| 2016/0015150 A1 * | 1/2016 | Casasanta, III | ...... | A46B 5/0095 401/4 |
| 2016/0045081 A1 * | 2/2016 | Kern | ...................... | A61H 7/003 15/22.4 |
| 2016/0183671 A1 * | 6/2016 | Skidmore | .............. | A61H 7/005 173/162.2 |
| 2016/0206087 A1 * | 7/2016 | Skidmore | .......... | A46B 15/0004 |
| 2016/0331106 A1 * | 11/2016 | Khormaei | ............. | A46B 13/02 |
| 2016/0331308 A1 * | 11/2016 | Zhou | .................... | A61B 5/0022 |
| 2017/0071321 A1 * | 3/2017 | Tang | .................... | A46B 13/023 |
| 2017/0128130 A1 * | 5/2017 | Giraud | ................ | A61H 9/0057 |
| 2017/0332850 A1 * | 11/2017 | Powell | .............. | A46B 15/0012 |
| 2017/0367543 A1 * | 12/2017 | Straka | ................ | A46B 15/0008 |
| 2018/0271337 A1 * | 9/2018 | Powell | .................. | A47K 7/043 |
| 2018/0295980 A1 * | 10/2018 | Boersma | ............. | A46B 15/003 |
| 2018/0325328 A1 * | 11/2018 | Wright | ................ | A46B 11/0062 |
| 2020/0129372 A1 * | 4/2020 | Tseng | .................... | H02J 7/0042 |
| 2021/0153638 A1 * | 5/2021 | Jeong | ...................... | A47K 7/04 |

* cited by examiner

END EFFECTOR WITH EMBEDDED POWER SOURCE

SUMMARY

In one aspect, the present disclosure provides an end effector generally including a base portion coupleable to a motor carried by an appliance that is separate from the end effector; and a battery disposed in the base portion configured to power an auxiliary component of the end effector.

In another aspect, the present disclosure provides a system generally including an appliance comprising a motor; and an end effector coupleable to the motor and configured to receive motion from the motor, the end effector comprising: a base portion coupleable to the motor; and a battery disposed in the base portion configured to power an auxiliary component of the end effector.

In accordance with any of the embodiments disclosed herein, the base portion generally includes an inner portion shaped to receive motion from the motor; and an outer portion disposed about the inner portion. In accordance with any of the embodiments disclosed herein, the battery is disposed in the outer portion. In accordance with any of the embodiments disclosed herein, the inner portion is shaped to move independently of the outer portion.

In accordance with any of the embodiments disclosed herein, the auxiliary component generally includes a light source positioned to emit light onto a user when the end effector is applied to the user.

In accordance with any of the embodiments disclosed herein, the end effector generally includes a plurality of contact members shaped to contact the user when the end effector is applied to the user. In accordance with any of the embodiments disclosed herein, the light source is disposed between contact members of the plurality of contact members. In accordance with any of the embodiments disclosed herein, the light source is configured to emit light through one or more of the plurality of contact members toward the user.

In accordance with any of the embodiments disclosed herein, the auxiliary component generally includes a source of motion disposed in the end effector configured to move the end effector when powered by the battery.

In accordance with any of the embodiments disclosed herein, the auxiliary component generally includes a formulation reservoir comprising a formulation for application to a user; and a pump configured to pump the formulation from the formulation reservoir to an application surface of the end effector.

In accordance with any of the embodiments disclosed herein, the battery is a rechargeable battery.

In accordance with any of the embodiments disclosed herein, the end effector generally includes a user input configured to operatively couple the auxiliary component to the battery to power the auxiliary component when the user input is actuated.

In accordance with any of the embodiments disclosed herein, the end effector generally includes an oscillation sensor configured to generate an oscillation signal indicative of oscillatory movement of the end effector; and a controller operatively coupled to the oscillation sensor and the auxiliary component; comprising logic that when executed by the controller causes the end effector to perform operations including actuating the auxiliary component based on received oscillation signal.

This foregoing summary is provided to introduce a selection of concepts in a simplified form that are further described below in the Detailed Description. This summary is not intended to identify key features of the claimed subject matter, nor is it intended to be used as an aid in determining the scope of the claimed subject matter.

Aspects and many of the attendant advantages of the claimed subject matter will become more readily appreciated as the same become better understood by reference to the following detailed description, when taken in conjunction with the accompanying drawings.

The detailed description set forth below in connection with the appended drawings, where like numerals reference like elements, is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

DETAILED DESCRIPTION

The following discussion provides examples of end effectors and systems for application of a therapy to a portion of a body. In the examples of end effectors and systems set forth in more detail below, several are provided that include end effectors including a power source, such as a battery, embedded in the end effector configured to power an auxiliary component of the end effector.

Certain conventional appliances coupleable to end effectors, such as brushes, applicators, dispensers, and the like, are configured to provide motion to the end effectors. However, many conventional appliances are not configured to supply electrical power to the end effectors coupled thereto. In this regard, such convention appliance are not configured to power components carried by the end effector, such as those configured to supply therapies to the portions of the body contacted by the end effector in addition to the motion provided by the appliance.

Toward that end, the present disclosure provides end effectors including a battery or other power source disposed in the end effector configured to supply electrical power to one or more auxiliary components also disposed in the end effector. As discussed further herein, such an auxiliary component is configured to provide therapy to a portion of a body contacted by the end effector in addition to therapy provided by motion of the end effector provided by a motor coupled thereto. As discussed further herein, such auxiliary components may be configured to provide therapies, such as light therapy, additional motion, formulations, and the like to the portion of the body contacted by the end effector.

In the following description, specific details are set forth in order to provide a thorough understanding of one or more embodiments of the present disclosure. It will be apparent to one skilled in the art, however, that embodiments of the present disclosure may be practiced without some or all of the specific details. Further, it will be appreciated that embodiments of the present disclosure may employ combinations of features described herein.

Figure 1A:
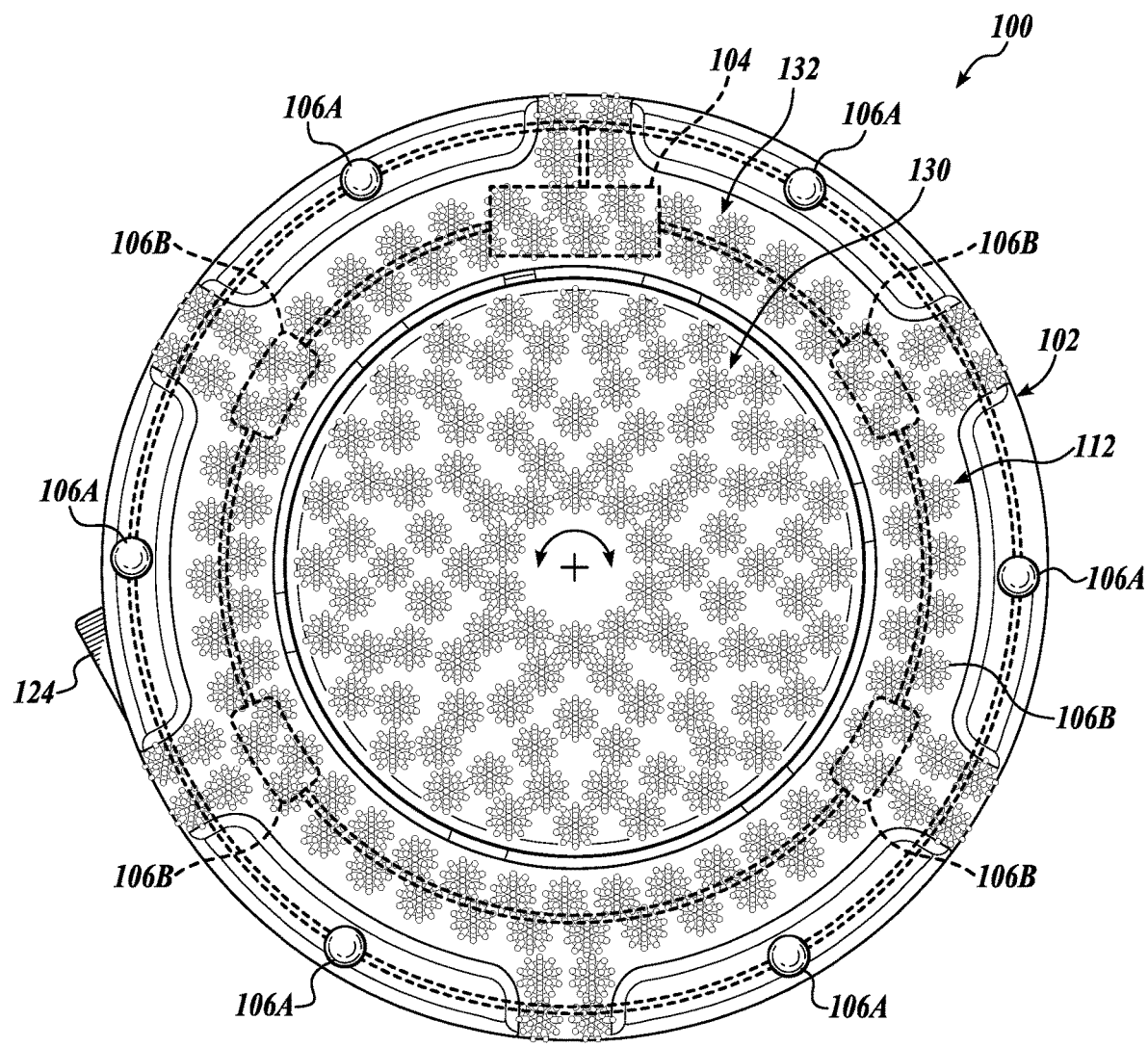
FIG. 1A is a top-down plan view of an end effector, in accordance with an embodiment of the disclosure.
Figure 1B:
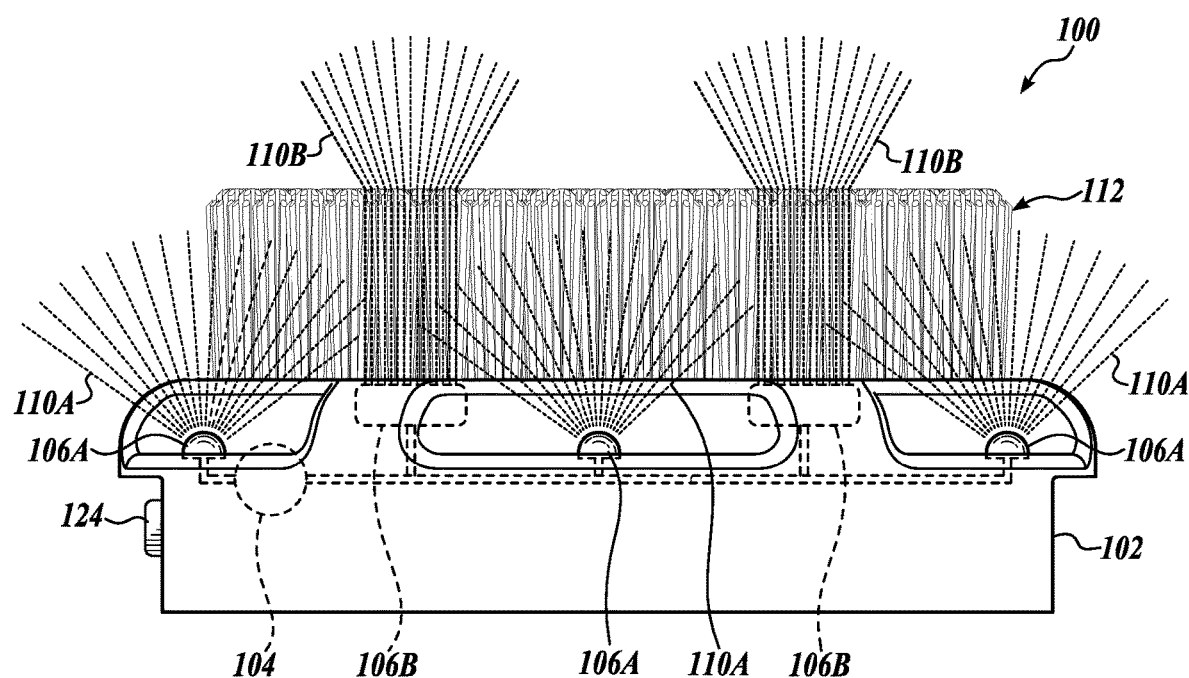
FIG. 1B is a side view in cross-section of the end effector of FIG. 1A.

Turning now to FIGS. 1A and 1B, there is shown an example of an end effector 100, in accordance with embodiments of the disclosure. FIG. 1A is a top-down plan view of the end effector 100, in accordance with an embodiment of the disclosure. FIG. 1B is a side view in cross-section of the end effector 100 of FIG. 1A.

Illustrated end effector 100 includes a base portion 102 coupleable to a motor carried by an appliance (not shown, see FIG. 3) that is separate from the end effector 100; and a battery 104 disposed in the base portion 102. As discussed further herein, the battery 104 may be configured to power an auxiliary component 106 of the end effector 100, where such an auxiliary component 106 is configured to provide a therapeutic, diagnostic, or other function in addition to such functions provided via movement received from the motor of the appliance. While battery 104 is discussed further herein, it will be understood that the end effector 100 can include other power sources, for example capacitors.

In an embodiment, the base portion 102 includes an inner portion 130 shaped to receive motion from the motor; and an outer portion 132 disposed about the inner portion 130. As shown, the outer portion 132 circumferentially surrounds the inner portion 130, although it will be understood that the outer portion 132 can merely partially surround the inner portion 130. In the illustrated embodiment, the inner portion 130 is shown to move independently from the outer portion 132. In this regard, the inner portion 130 may be configured to, for example, provide a cleansing effect on the portion of the body contacted by the end effector 100 as it receives motion from a motor of an appliance coupled thereto.

In the illustrated embodiment, the battery 104 is disposed within the outer portion 132 of end effector 100. Some motors of appliances are sensitive to masses coupled thereto, such as masses of end effectors. In that regard, by disposing the battery 104 in the outer portion 132, the attendant mass of the battery 104 does not affect, for example, oscillation of the inner portion 130. In an embodiment, the outer portion 132 is configured to remain stationary as the inner portion 130 receives motion from the motor.

In the illustrated embodiment, the end effector 100 is a brush 100 including a plurality of contact members 112, shown here as bristles 112, configured to contact the user when the end effector 100 is applied to the user. Such bristles 112 are configured to provide a cleansing, massaging, and/or stimulating effect when motion from the motor is received. While a brush 100 including bristles 112 is discussed and shown, it will be understood that the end effectors 100 of the present disclosure encompass applicators, heaters, exfoliators, massagers, brushes, and the like.

The end effector 100 further includes an auxiliary component 106 powered by the battery 104 disposed in the end effector 100. Such an auxiliary component 106 is configured to provide a therapeutic, diagnostic, or other effect on the portion of the body contacted by end effector 100 in addition or instead of the effects provided by motion received from the motor of an appliance coupled to the end effector 100. In the illustrated embodiment, the auxiliary component 106 includes a number of light sources 106A and 106B positioned to emit light toward a user when the end effector 100 is applied to the user. Such light sources 106A and 106B may be configured to emit light having wavelengths configured to provide an antiaging effect, such as light having wavelengths in a range of about 400 nm to about 1,200 nm. In an embodiment, the light sources 106A and 106B include light sources selected from the group consisting of light-emitting, diodes, incandescent bulbs, fluorescent lamps, and combinations thereof.

The illustrated end effector 100 includes a first plurality of lights 106A operatively coupled to the battery 104 and disposed about a periphery of base portion 102. As shown, the first plurality of light sources 106A is disposed between the plurality of contact members 112. In this regard, the first plurality of light sources 106A is configured to emit light 110A toward a user from between the plurality of contact members 112 when the end effector 100 contacts the user.

The end effector 100 is further shown to include a second plurality of light sources 106B shown disposed within base portion 102. As shown, the second plurality of light sources 106B is configured to emit light 110B through one or more of the plurality of contact members 112. In an embodiment, the one or more of the plurality of contact members 112 are light pipes configured to transmit the light 110B from the second plurality of light sources 106B. In this regard, the end effector 100 is configured to emit light 110B onto a portion of the body contacted by the end effector 100 and to contact the portion of the body with at least some of the plurality of contact members 112, thereby providing, for example, at least two modes of therapy to the portion of the body.

In an embodiment, one or more of the first plurality of light sources 106A and the second plurality of light sources 106B is configured to emit light 110A and/or 110B, respectively, having an intensity sufficient to provide a therapeutic effect to the portion of the body contacted by the end effector 100, such as an anti-aging effect. In an embodiment, such intensity is configured to provide a therapeutic affect despite any attenuation of an intensity of light 110A and/or 110B due to, for example, a formulation, such as a cleansing solution, disposed between the pluralities of light sources 106A and 106B and the portion of the body.

While the pluralities of light sources 106A and 106B are shown disposed about a periphery of the base portion 102 and within the outer portion 132 of the end effector 100, respectively, it will be understood that an auxiliary component 106 including a light source (not shown) may also be disposed within other portions of the end effector 100, such as in the inner portion 130 of the end effector 100.

The end effector 100 is shown to include a user input 124 configured to operatively couple the auxiliary component 106 with the battery 104 that powers the auxiliary component 106 when the user input 124 is actuated. In the illustrated embodiment, the user input 124 is a button configured to be actuated by physical input from a user, such as from a finger, but other configurations of the user input 124 are also possible. By actuating the user input 124, the auxiliary component 106, pluralities of light sources 106A and 106B are activated to emit light 110A and 110B, respectively.

In an embodiment, the battery 104 is a rechargeable battery 104 configured to receive electrical power from an external source when, for example, electrical power of the rechargeable battery 104 has been depleted. In another embodiment, the battery 104 is a single-use battery 104. In an embodiment, a useable life of the single-use the battery 104 corresponds to an intended use interval of the end effector 100. As the end effector 100 is used over time, it may become worn, dirty, or otherwise unsuitable to provide its intended therapeutic benefits. In this regard, as the single-use battery 104 is used up and runs out of power, the end effector 100 may be configured to signal to a user that the end effector 100 is ready for replacement, cleaning, reconditioning, and the like.

Figure 2A:
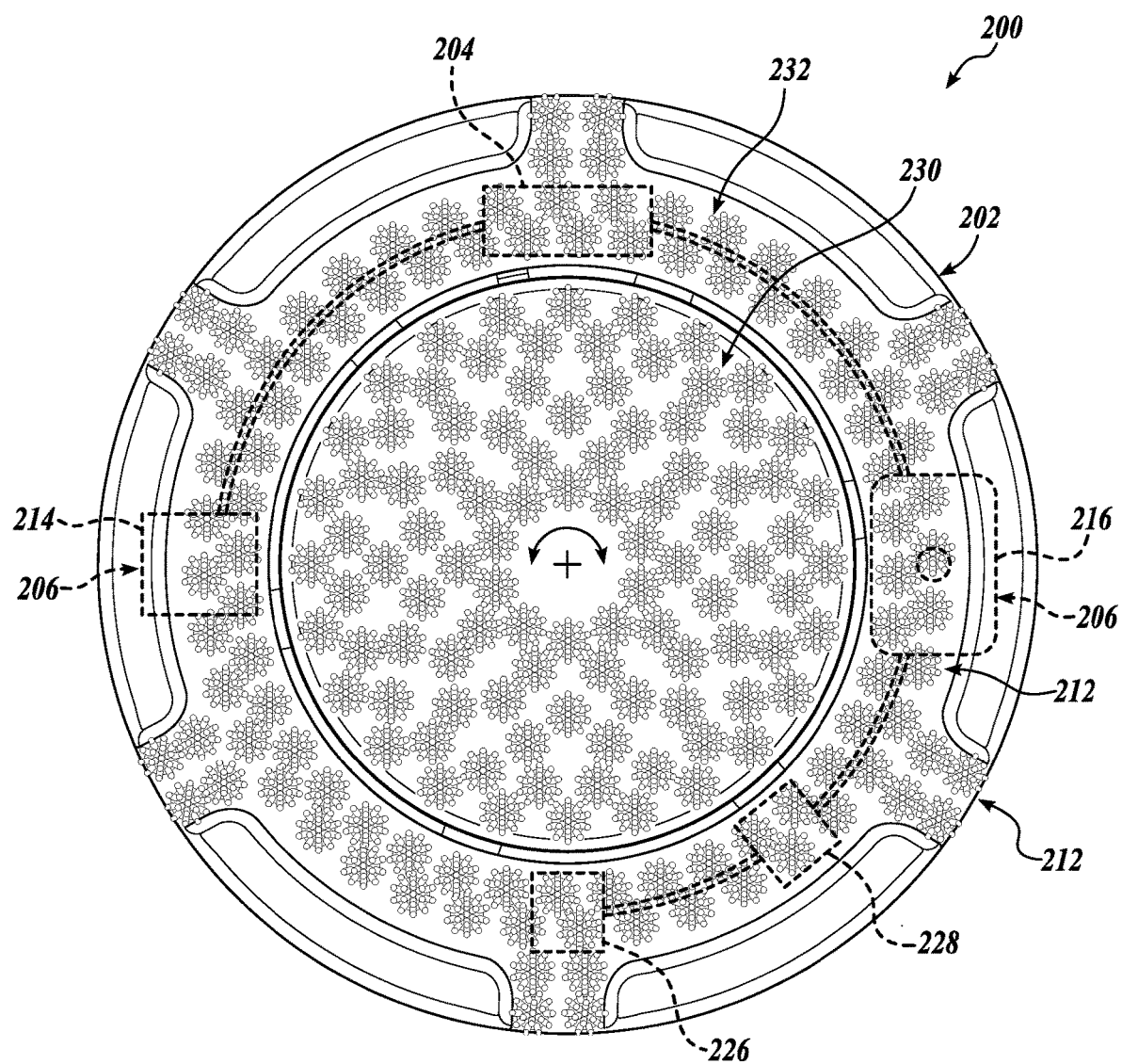
FIG. 2A is a top-down plan view of another end effector, in accordance with an embodiment of the disclosure.
Figure 2B:
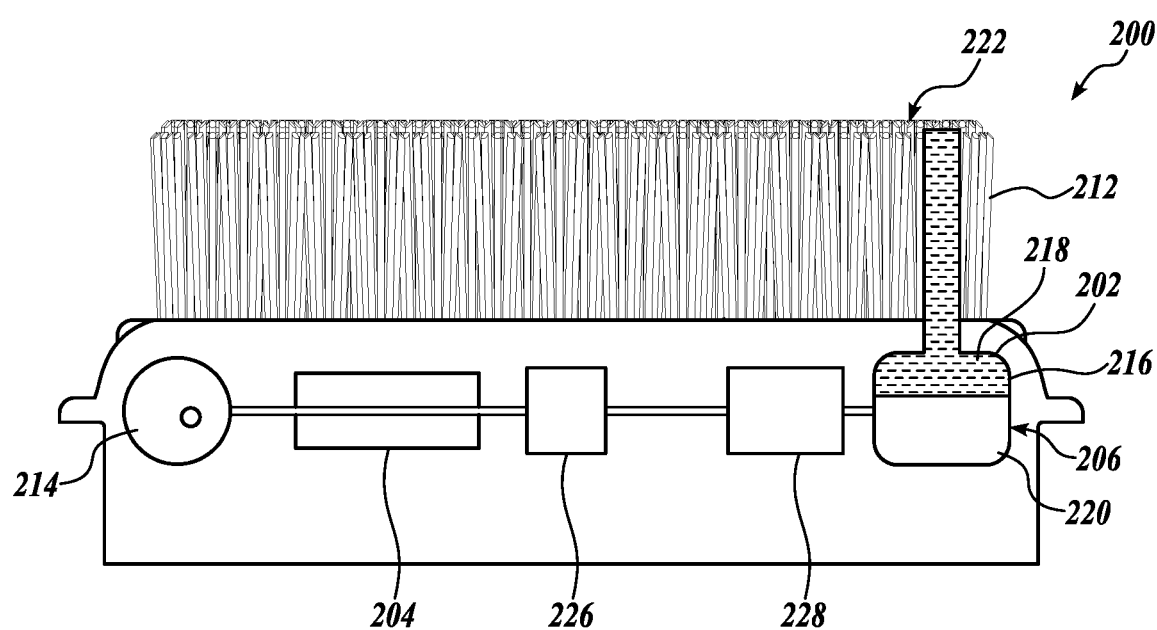
FIG. 2B is a side view in cross-section of the end effector of FIG. 2A.

In an embodiment, the auxiliary components of the end effectors of the present technology are configured to provide two or more therapeutic or other effects. In this regard, attention is directed to FIGS. 2A and 2B in which an end effector 200 according to an embodiment of the disclosure is illustrated. FIG. 2A is a top-down plan view of the end effector 200, in accordance with an embodiment of the disclosure. FIG. 2B is a side view in cross-section of the end effector 200.

As shown, the end effector 200 includes a base portion 202 coupleable to a motor carried by an appliance (not shown, see FIG. 3) that is separate from the end effector 200; and a battery 204 disposed in the base portion 202 and configured to power an auxiliary component 206 of the end effector 200. The base portion 202 includes an inner portion 230 shaped to receive motion from the motor; and an outer portion 232 disposed about the inner portion 230. As discussed above with respect to FIGS. 1A and 1B, such a configuration may be suitable to provide, for example, oscillation of the inner portion 230 from motion received from the motor relatively unaffected by a mass of the battery 204 disposed on the outer portion 232 of end effector 200. A shown, the inner portion 230 and outer portion 232 are shown to include a plurality of contact members 212 configured to contact a portion of a body contacted by end effector 200.

In the illustrated embodiment, the end effector 200 includes an auxiliary component 206 including a source of motion 214 carried by the base portion 202. The source of motion 214 is operatively coupled to battery 204 to receive electrical power therefrom. In this regard, the auxiliary component 206 including source of motion 214 is configured to provide motion in addition to motion received by the end effector 200 from a motor of an appliance coupled to the end effector 200 in a direction or in a plane not provided by the motor. For example, the motor carried by the appliance may be configured to oscillate the end effector 200 about an axis and/or plane of the end effector 200, whereas source of motion 214 is configured to move end effector 200 about another axis or plane of the end effector 200. In this regard, auxiliary component 206 of end effector 200 is configured to provide a therapeutic effect in addition to those provided by an appliance coupled thereto.

The auxiliary component 206 of the end effector 200 is further shown to include a formulation reservoir 216 comprising a formulation 218 for application to a user; and a pump 220 configured to pump the formulation 218 from the formulation reservoir 216 to an application surface 222 of the end effector 200. As shown, the pump 220 is operatively coupled to the battery 204 and configured to receive electrical power therefrom to pump the formulation 218 from the formulation reservoir 216 to the application surface 222. In this regard, the auxiliary component 206 is configured to direct the formulation 218 to the application surface 222 for application to a portion of the body contacted by the end effector 200. In an embodiment, the formulation 218 is selected from the group consisting of a cleansing formulation, a moisturizer, an exfoliating formulation, and combinations thereof.

In the illustrated embodiment, the end effector 200 further includes a motion sensor 226, such as an oscillation sensor 226, configured to generate a movement signal, such as an oscillation signal, indicative of movement of the end effector 200. In this regard, as end effector 200 is oscillated, such as due to movement received from the motor of an appliance coupled to the end effector 200, the oscillation signal is generated. End effector 200 further includes a controller 228 operatively coupled to the oscillation sensor 226 and auxiliary component 206. In an embodiment, the controller 228 includes logic that when executed by the controller 228 causes the end effector 200 to perform operations. In an embodiment, such operations include actuating the auxiliary component 206 based on received oscillation signal. In this regard, as the end effector 200 is moved, such as oscillated, due to motion received from a motor of an appliance coupled to the end effector 200, the auxiliary component 206 may be activated. Such activation of the auxiliary component 206 in conjunction with motion of the end effector 200 is configured to provide therapeutic effects of motion of the end effector 200 due to coupling with the motor and therapeutic effects from the auxiliary component 206.

Figure 4A:
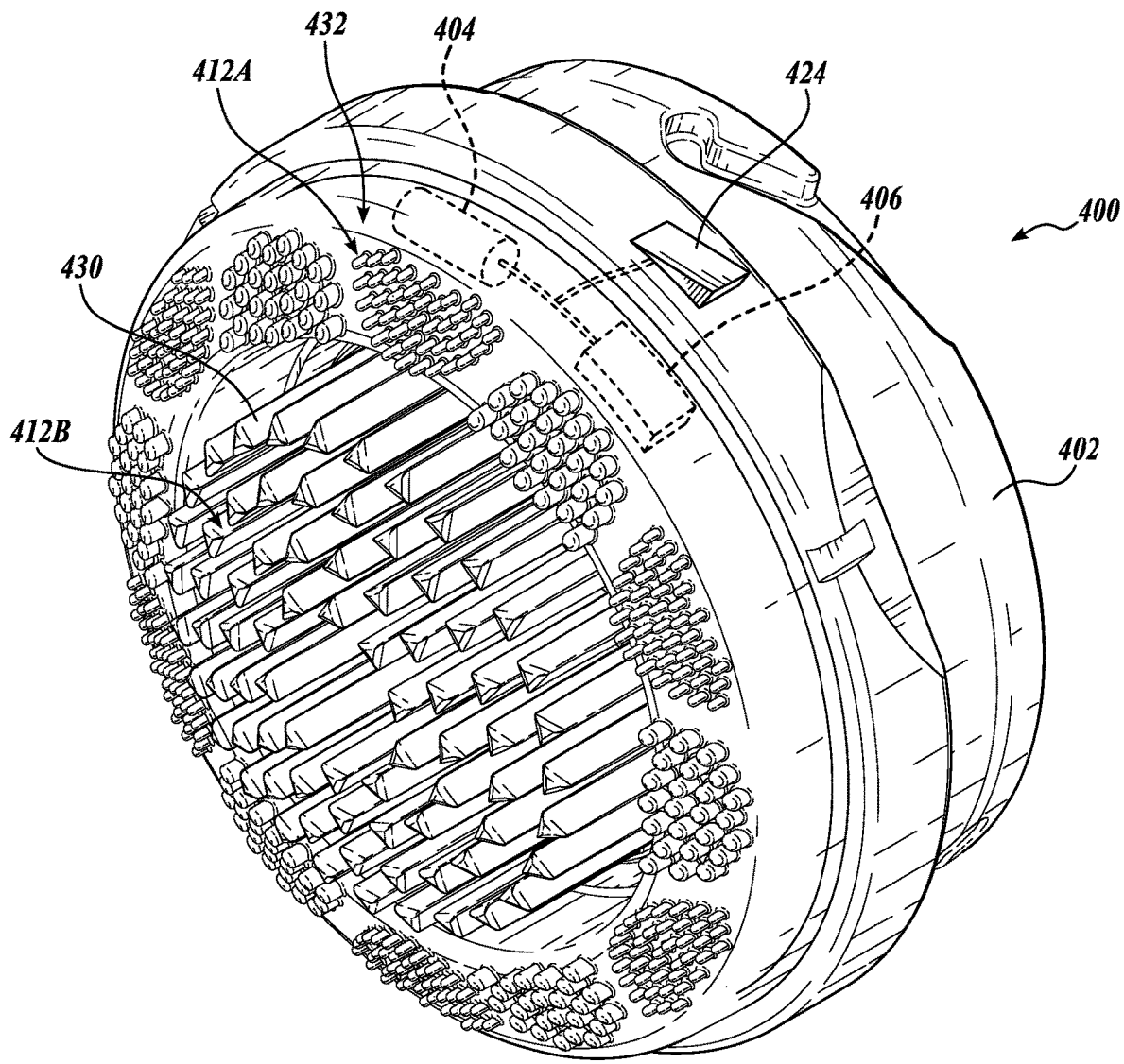
FIG. 4A is a perspective view of an end effector, in accordance with an embodiment of the disclosure.
Figure 4B:
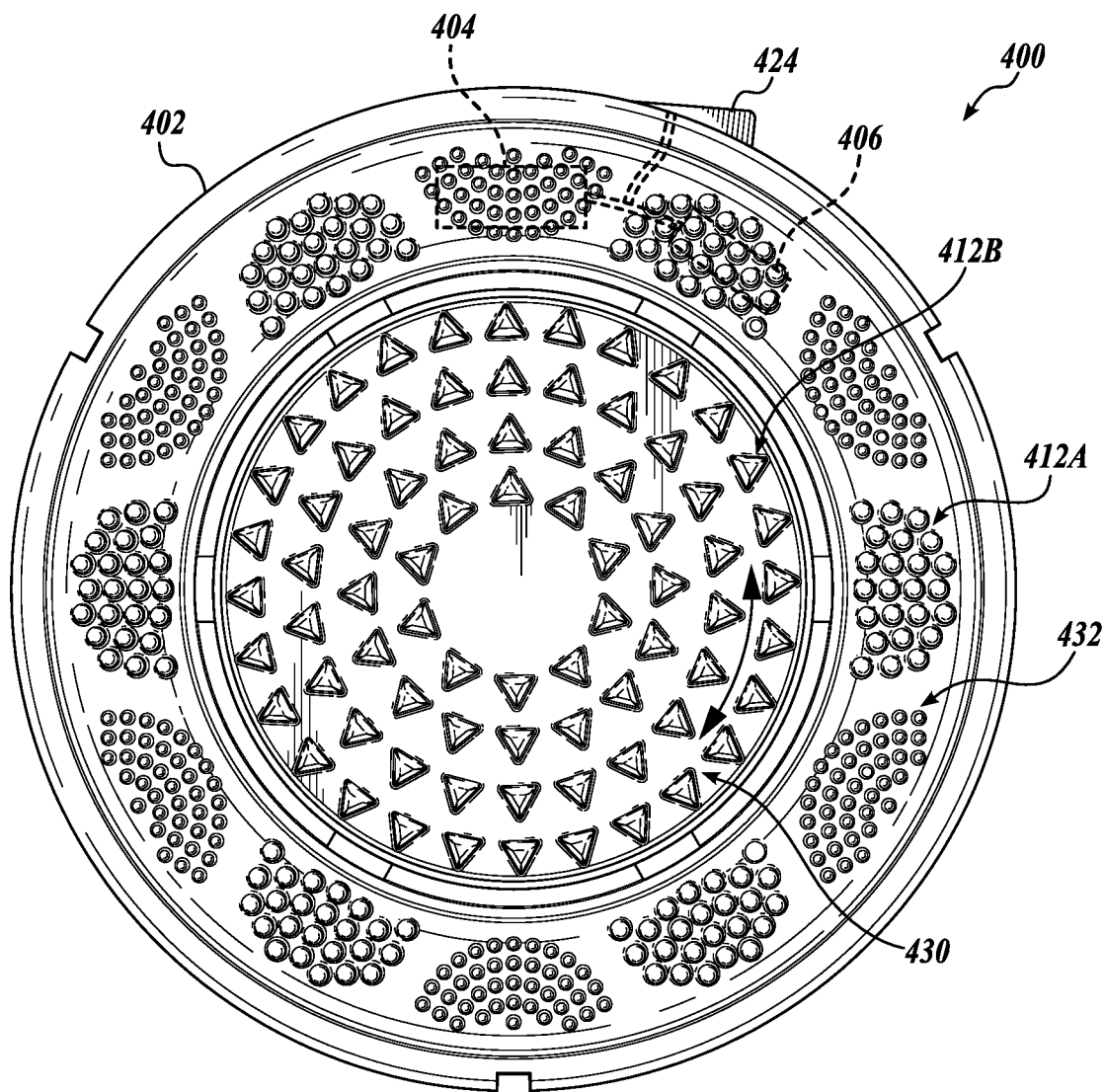
FIG. 4B is a top-down plan view of the end effector of FIG. 4A.

In an embodiment, the end effectors of the present technology include exfoliators coupleable to a motor of an appliance. In that regard, attention is directed to FIGS. 4A and 4B illustrating an end effector 400, in accordance with an embodiment of the disclosure. FIG. 4A is a perspective view of the end effector 400. FIG. 4B is a top-down plan view of the end effector 400.

Illustrated end effector 400 includes a base portion 402 coupleable to a motor carried by an appliance (see FIG. 3) that is separate from the end effector 400; and a battery 404 disposed in the base portion 402 configured to power an auxiliary component 406 of the end effector 400. As above, end effector 400 is an exfoliator 400 suitable to remove dead skin from a portion of a user's body contacted by the end effector 400. In this regard, the end effector 400 includes a number of contact members 412 configured to contact a portion of a user's body and remove dead skin therefrom, such as through motion of the end effector 400 received from a motor (see FIG. 3) coupled to the end effector 400.

As shown, the end effector 400 includes an inner portion 430 configured to receive motion from the motor; and an outer portion 432 disposed about the inner portion 430. In the illustrated embodiment, the battery 404 is carried by the outer portion 432. As above, by disposing a mass of the battery 404 in the outer portion 432 of the end effector 400, which is configured to move independently of the inner portion 430, a motor coupled to the end effector 400 is dampened less than if the battery 404 were disposed in the inner portion 430. As above, motors of certain appliances are sensitive to masses coupled thereto. By disposing the battery 404 in the outer portion 432, the end effector 400 may be suitable to couple to a wider range of appliances.

As above, the end effector 400 includes a number of contact members 412 configured to contact a portion of a user's body contacted by the end effector 400. As shown, the end effector 400 includes a first plurality of contact members 412A carried by the outer portion 432 and a second plurality of contact members 412B carried by the inner portion 430. In an embodiment, the first plurality of contact members 412A, carried by the outer portion 432, are configured to massage the portion of the user's body contacted by the end effector 400. In an embodiment, the second plurality of contact members 412B, carried by the inner portion 430 are configured to receive motion from a motor coupled to the end effector 400. In that regard, the second plurality of contact members 412B are also configured to scrape, abrade, and/or scour a portion of the body contacted by the end effector 400 to remove dead skin therefrom.

The outer portion 432 of the end effector 400 is shown to further carry the auxiliary component 406, which is operatively coupled to the battery 404 and receives power therefrom. In the illustrated embodiment, the auxiliary component 406 is a source of motion 406. As above, such a source of motion 406 may be configured to provide motion different from and/or in addition to motion received from a motor coupled to the end effector 400. In the illustrated embodiment, the source of motion 406 is carried by the outer portion 432, which, in an embodiment, does not receive motion from a motor coupled thereto. In that regard, the source of motion 406 may be configured to provide motion, such as vibratory motion, to the outer portion 432 of the end effector 400, suitable to massage the portion of the body contacted by the end effector 400.

The end effector 400 further includes a user input 424 configured to operatively couple the auxiliary component 406 to the battery 404 to power the auxiliary component 406 when the user input 424 is actuated. In the illustrated embodiment, the user input 424 is a button 424 configured to be actuated, for example, by a finger. While a button 424 is described with respect to FIG. 4, it will be understood that other user inputs including sensors are possible, such as motion sensor 226 discussed further herein with respect to FIGS. 2A and 2B.

Figure 3:
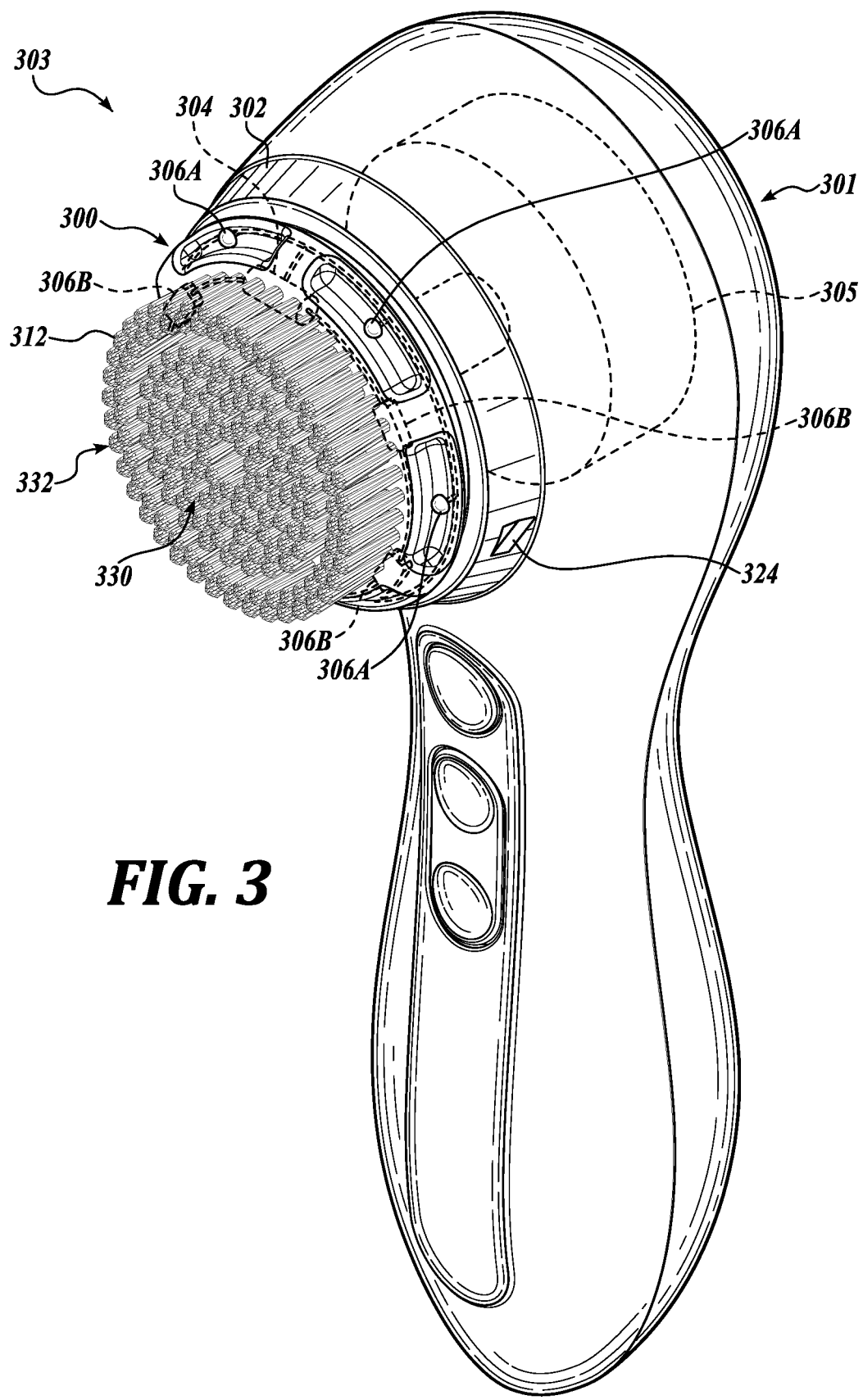
FIG. 3 is a perspective view of a system, in accordance with an embodiment of the disclosure.

Turning now to FIG. 3, the present disclosure provides a system 303 including an appliance 301 and an end effector 300, as described herein, coupleable to the appliance 301, such as through the base portion 302. FIG. 3 is a perspective view of a system 303 shown to include an appliance 301 comprising a motor 305; and an end effector 300 coupleable to the motor 305 and configured to receive motion from the motor 305. In an embodiment, the end effector 300 is an example of end effectors like the end effectors 100 and/or 200.

The illustrated end effector 300 includes a base portion 302 coupleable to the motor 305; and a battery 304 disposed in the base portion 302 configured to power an auxiliary component 306 of the end effector 300. As shown, the end effector 300 is coupled to the motor 305 of appliance 301 to receive motion, such as oscillatory motion.

In an embodiment, the appliance 301 does not include an electrical connection configured to provide electrical power from the appliance 301 to the end effector 300. In this regard, the end effector 300 is configured to power the auxiliary component 306 that provides therapy to a portion of a body contacted by the end effector 300 in addition to motion of the end effector 300 received from the motor 305 of the appliance 301.

In the illustrated embodiment, the end effector 300 includes an inner portion 330 shaped to receive motion from the motor 305; and an outer portion 332 disposed about the inner portion 330, as discussed further herein with respect to FIGS. 1A, 1B, 2A, and 2B. As shown, the battery 304 is disposed in the outer portion 332, which is configured to move independently of the inner portion 330. Because a mass of battery 304 is disposed in the outer portion 332, motion of the inner portion 330 is not dampened or inhibited by such mass.

The illustrated end effector 300 is shown to include an auxiliary component 306, shown here to include a first plurality of light sources 306A and a second plurality of light sources 306B. As discussed above with respect to FIGS. 1A and 1B, such pluralities of light sources 306A and 306B may be configured to emit light onto a portion of a body contacted by the end effector 300, thereby providing, for example, an anti-aging effect to the portion of the body. In this regard, the auxiliary component 306 is configured to provide therapeutic effect in addition therapeutic effect from motion received by the end effector 300 from motor 305.

As discussed above with respect to FIGS. 2A and 2B, such an auxiliary component 306 can include, for example, a source of motion (shown in FIGS. 2A and 2B) in addition to motion received from motor 305. In an embodiment, the source of motion, such as source of motion 214, is configured to provide motion different from motion received by motor 305 to the end effector 300. In an embodiment, motor 305 is configured to provide motion such as oscillatory motion, vibratory motion, rotational motion, and the like. In an embodiment, source of motion is configured to provide motion to the end effector 300 about a different axis than, in a different direction than, and/or about a different plane of the end effector 300 than motion received by the end effector 300 from motor 305. Such different motion provided by the source of motion may be configured to provide different and/or additional therapeutic effects than motion received by the end effector 300 from motor 305. In an embodiment, the source of motion is configured to augment motion provided by the motor 305 to the end effector 300, such as by providing motion in the same direction as and/or about the same axis and/or plane of the end effector 300.

The auxiliary component 306 can also include a formulation reservoir (see FIGS. 2A and 2B) comprising a formulation for application to a user; and a pump (see FIGS. 2A and 2B) configured to pump the formulation from the formulation reservoir to an application surface 322 of the end effector 300. As discussed further above with respect to FIGS. 2A and 2B, such a formulation can include a formulation selected from the group consisting of a cleansing formulation, a moisturizer, an exfoliating formulation, and combinations thereof. By pumping the formulation onto an application surface 322 of the end effector 300, such as a surface of a plurality of contact members 312, the formulation may be applied to a portion of the body contacted by the end effector 300.

The end effector 300 is shown to further include a user input 324 operatively coupled to the battery 304 and the auxiliary component 306. As discussed above with respect to FIGS. 1A and 1B, by actuating the user input 324, the auxiliary component 306 and the battery 304 are operatively coupled to supply electrical power to the auxiliary component 306. As discussed further above with respect to FIGS. 2A and 2B, such a user input 324 may be replaced and/or augmented by motion sensor, such as motion sensor 226, and a controller coupled thereto, where the controller is configured to activate the auxiliary component 306 when the motion sensor is moved, such as by motor 305.

It should be noted that for purposes of this disclosure, terminology such as "upper," "lower," "vertical," "horizontal," "inwardly," "outwardly," "inner," "outer," "front," "rear," etc., should be construed as descriptive and not limiting the scope of the claimed subject matter. Further, the use of "including," "comprising," or "having" and variations thereof herein is meant to encompass the items listed thereafter and equivalents thereof as well as additional items. Unless limited otherwise, the terms "connected," "coupled," and "mounted" and variations thereof herein are used broadly and encompass direct and indirect connections, couplings, and mountings. The term "about" means plus or minus 5% of the stated value.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

While illustrative embodiments have been illustrated and described, it will be appreciated that various changes can be made therein without departing from the spirit and scope of the invention.

The embodiments of the invention in which an exclusive property or privilege is claimed are defined as follows:

1. A brush system comprising:
    an appliance comprising a motor; and
    an end effector removably coupleable to the motor and the appliance and configured to receive motion from the motor, the end effector comprising:
        a base portion coupleable to the motor, the base portion comprising an inner portion and an outer portion;
        a source of motion configured to provide vibration motion to the end effector in a direction or plane not provided by the motor; and
        a battery disposed in the base portion configured to power an auxiliary component of the end effector and the source of motion,
        wherein the appliance does not include an electrical connection configured to provide electrical power between the appliance and the end effector, wherein the motor is configured to rotate the inner portion.

2. The brush system of claim 1, the end effector further comprising a plurality of contact members shaped to contact the user when the end effector is applied to the user.

3. The brush system of claim 2, wherein the end effector further comprising a light source is disposed between contact members of the plurality of contact members.

4. The brush system of claim 3, wherein the light source is configured to emit light through one or more of the plurality of contact members toward the user.

5. The brush system of claim 1, wherein the battery is a rechargeable battery.

6. The brush system of claim 1, the end effector further comprising a user input configured to operatively couple the auxiliary component to the battery to power the auxiliary component when the user input is actuated.

7. The brush system of claim 1, the end effector further comprising:
    an oscillation sensor configured to generate an oscillation signal indicative of oscillatory movement of the end effector; and
    a controller operatively coupled to the oscillation sensor and the auxiliary component;
    comprising logic that when executed by the controller causes the end effector to perform operations comprising:
        actuating the auxiliary component based on received oscillation signal.

8. The brush system of claim 1, wherein the battery is disposed in the outer portion.

9. The brush system of claim 1, wherein the inner portion is shaped to move independently of the outer portion.

10. The brush system of claim 1, wherein the auxiliary component comprises a light source positioned to emit light onto a user when the end effector is applied to a user.

11. The brush system of claim 1, wherein the auxiliary component comprises:
    a formulation reservoir comprising a formulation for application to a user; and
    a pump configured to pump the formulation from the formulation reservoir to an application surface of the end effector.

12. The brush system of claim 1, wherein the outer portion is configured to remain stationary as the inner portion receives an oscillatory motion from the motor.

* * * * *